United States Patent [19]

Horwath et al.

[11] Patent Number: 4,492,755
[45] Date of Patent: Jan. 8, 1985

[54] PROCESS FOR ISOMERIZING L-MANNOSE TO L-FRUCTOSE

[75] Inventors: Robert O. Horwath, Westport; William J. Colonna, Wilton, both of Conn.

[73] Assignee: Nabisco Brands, Inc., Parsippany, N.J.

[21] Appl. No.: 393,844

[22] Filed: Jun. 30, 1982

[51] Int. Cl.$^3$ .................. C12P 19/24; C12N 15/00; C12N 9/90; C12R 1/19; C12R 1/22; C12R 1/25
[52] U.S. Cl. ................. 435/94; 435/172.1; 435/233; 435/849; 435/852; 435/857
[58] Field of Search .............. 435/94, 172, 233, 234, 435/253

[56] References Cited

U.S. PATENT DOCUMENTS 3,813,318  5/1974  Armbruster et al. .......... 435/233 X
4,355,103 10/1982  Boguslawski et al. ......... 435/234 X

OTHER PUBLICATIONS

Wang et al., Fermentation and Enzyme Technology, 1979, pp. 47-49.
Mayo et al., Carbohydrate Research, vol. 8, pp. 344-347, (1968).

Primary Examiner—Lionel M. Shapiro
Attorney, Agent, or Firm—Richard Kornutik

[57] ABSTRACT

Process for preparing L-fructose from L-mannose by contacting L-mannose with L-mannose isomerase produced by a mutant microorganism selected from the group consisting of the genera Escherichia, Lactobacillus, and Klebsiella cultivated in the absence of an inducing sugar.

6 Claims, No Drawings

PROCESS FOR ISOMERIZING L-MANNOSE TO L-FRUCTOSE

BACKGROUND OF THE INVENTION

This invention relates to a process for preparing L-fructose alone or in admixture with other L-sugars, such as L-mannose and L-glucose.

L-sugars are useful as sweetening agents because, as disclosed in U.S. Pat. No. 4,262,032, they are sweet like the D-sugars, but unlike D-sugars, L-sugars are either not metabolized by the body or are metabolized to a lesser extent than the D-sugars. These features make L-sugars desirable as sweeteners for individuals wishing to reduce caloric-intake or for individuals unable to metabolize common sugar sweetening agents without detrimental effects, e.g., diabetics. Another advantage associated with L-sugars include the absence of an objectionable aftertaste commonly experienced with artificial sweeteners such as saccharin and the cyclamates. However, as desirable as the L-sugars are in the foregoing respects, their relative scarcity in nature, particularly L-glucose and L-fructose, the laevo counterparts of the two monosaccharide sweeteners most commonly used today, has prevented their widespread use in foods and beverages.

Mayo, et al., "Enzymatic Preparation of L-fructose", *Carbohyd. Res.*, 8 (1968), pp. 344–347, the contents of which are incorporated by reference herein, describes the enzymatic isomerization of L-mannose to L-fructose by employing L-mannose isomerase isolated from *Klebsiella aerogenes* cultivated in a nutrient medium containing L-rhamnose which is required to induce the microorganism to produce the enzyme. The need for L-rhamnose, a scarce and expensive L-sugar, imposes a considerable limitation on the practical usefulness of the Mayo, et al. process.

SUMMARY OF THE INVENTION

In accordance with the present invention, L-mannose is isomerized to L-fructose by employing L-mannose isomerase isolated from or present in a mutant strain or microorganism which is capable of producing L-mannose isomerase in the absence of an inducer, and is selected from one of the genera selected from the group consisting of Escherichia, Lactobacillus, and Klebsiella.

The foregoing mutant strain of microorganism is obtained by mutagenizing a culture of a selected microorganism by exposure to chemical or physical mutagens such as ethyl methane-sulfonate, nitrosoguanidine or 8-azaguanine, or by irradiation with ultraviolet light, gamma-rays or X-rays. An example of obtaining a mutant strain of a microorganism capable of producing xylose isomerase without an inducer by ultra-violet irradiation is found in U.S. Pat. No. 3,813,318 to Armbruster, et al., the contents of which are incorporated by reference herein. Methods generally known in the art are used to determine which individual colonies from the resulting culture are capable of producing L-mannose isomerase in the absence of an inducer. The mutant microorganisms which have the desired characteristic are isolated by conventional microbiological techniques.

DESCRIPTION OF THE PREFERRED EMBODIMENTS

The starting L-sugar for the process herein, L-mannose, can be obtained by chemical conversion of L-arabinose, a naturally occurring sugar which is available in significant quantities from sugar beet pulp by the method described in *Chemical Abstracts:* 142135v, Vol. 75, 1971 (Czech. Pat. No. 137,537), the contents of which are incorporated by reference herein. According to this method, dry sugar beet pulp is treated with sulfuric acid to obtain an extract solution which is subsequently fermented, evaporated and filtered. L-arabinose is thereafter crystallized from the resulting filtrate.

L-mannose can be obtained from L-arabinose by the method of Sowden and Fischer, *J.A.C.S.*, Vol. 69 (1947), pp. 1963–1965, the contents of which are incorporated by reference herein. In accordance with this method, L-arabinose is condensed with nitromethane in the presence of sodium methoxide to provide sodium salts of the nitroalcohols. The sodium salts are readily converted to the corresponding sugars by means of the Nef reaction. The Sowden-Fischer conversion of L-arabinose to the L-mannose starting material of this invention is represented by the following equations:

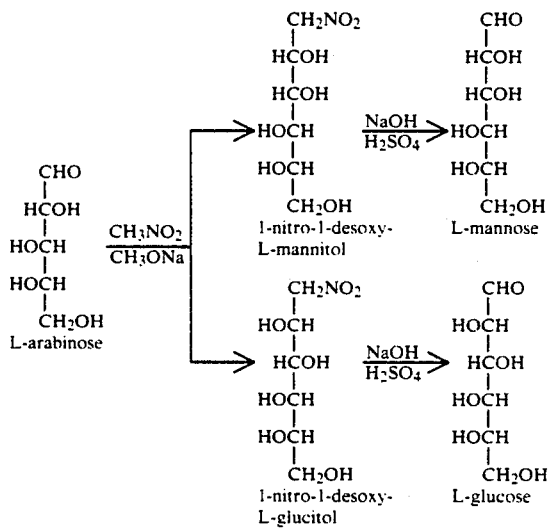

In addition to the Sowden-Fischer method, L-mannose can also be made by the Kiliani-Fischer synthesis which is described in, amongst others, *Organic Chemistry* by Morrison and Boyd (2d ed. 1966), pp. 990–991, the contents of which are incorporated by reference herein. According to the Kiliani-Fischer method, L-arabinose is converted into two glyconic acids of the next higher carbon number by condensation with hydrocyanic acid and hydrolysis of the resulting cyanohydrins. The glyconic acids are then reduced to the corresponding aldoses. The Kiliani-Fischer synthesis of L-mannose from L-arabinose is illustrated by the following equations:

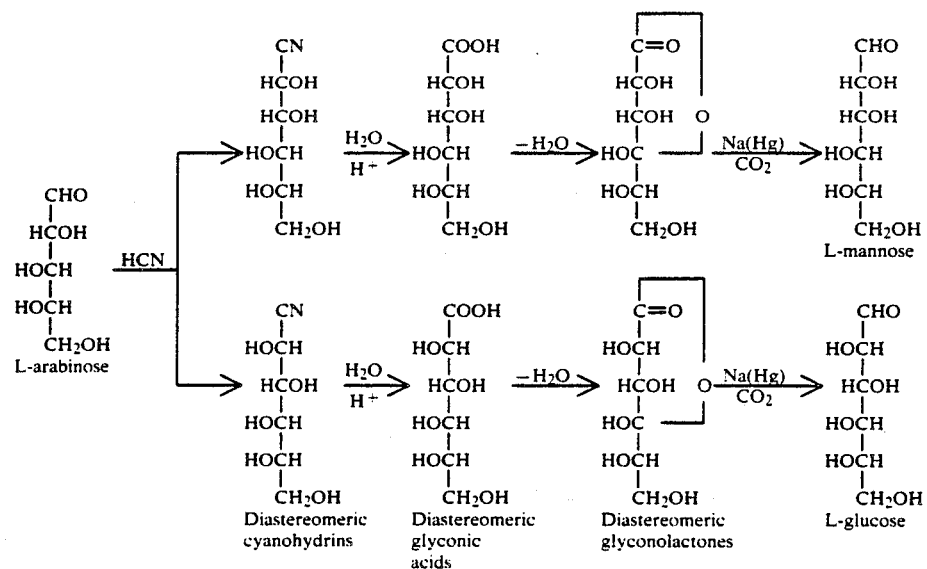

Both synthetic procedures provide L-mannose in admixture with L-glucose. The L-glucose can be separated from the L-mannose, e.g., by differential crystallization in either a free or derivatized state, or by separation using ion-exchange techniques. However, for reasons of economy, it is preferred to employ the mixture of the two sugars in the present invention without attempting to isolate or concentrate the L-mannose before effecting the enzyme isomerization of L-mannose to L-fructose.

To obtain the L-isomerase enzyme utilized herein, one can use any microorganism which produces L-mannose isomerase, e.g., *Escherichia coli, Lactobacillus plantarium,* or *Klebsiella aerogenes.* However, *Klebsiella aerogenes* is preferred as the parent strain because it is known to be a good source of L-mannose isomerase.

The selected microorganism is mutagenized by exposure to chemical or physical mutagens such as ethyl methane-sulfonate, nitrosoguanidine, or 8-azaguanine, or by irradiation with ultraviolet light, gamma-rays or X-rays.

The treated cells are then propagated by generally known methods until the cell number has increased at least about 25 fold. The treated cells are plated out, and each colony is tested by art-recognized procedures for L-mannose isomerase activity, e.g., the mutagenized colonies can be individually cultivated in test tubes, and, subsequently, by known methods cells from each colony are harvested, lysed and tested for the presence of L-fructose. Since the medium on which the colonies are grown does not contain L-rhamnose or any other L-sugar to induce the production of L-mannose isomerase enzyme, only that colony having the desired characteristics will show a positive enzyme reaction.

A very preferred method of testing for L-mannose isomerase activity is to press a circular disc of filter paper moistened with 0.16M Tris-HCl buffer (pH 7.6) containing 67 mM $CoCl_2$ and a permeabilizing agent such as disodiumethylenediaminetetraacetic acid and lysozyme mixture. Triton X-100, Tween 80, cetyltrimethylammonium bromide, deoxycholic acid, and the like, onto the plates of treated cells to pick up the microbial colonies by adsorption. Since L-mannose is intracellular, a permeabilizing agent is required so that L-mannose will freely penetrate into the cells to react with the enzyme, and so that L-fructose formed therefrom can freely diffuse out of the cells where it can be detected. A "sandwich" of the microbes is formed by placing the first disc of filter paper colony-side down onto a second disc of filter paper moistened with the above solution containing 10% L-mannose.

The paper sandwich is pressed between two clean glass plates and incubated at 30° C. for a period of time necessary for isomerization of L-mannose to L-fructose to occur. The paper sandwich is disassembled and air-dried. The papers are then sprayed with acidic naphthoresorcinal for ketose detection. The development of pink spots is a positive test for keto-sugar, i.e., L-fructose and, therefore, L-mannose isomerase. Colonies corresponding to these positive zones on the filter paper are then located by reference to the original master plates and isolated by conventional microbiological techniques.

The desired colonies are then grown from about 12 to about 72 hours at 25° to 35° C. at a pH between 6 to 8 under conditions generally known to be suitable for the species. For example, *Klebsiella aerogenes* is ordinarily grown under aerobic conditions in an aqueous mineral medium containing sodium phosphate, potassium phosphate, and traces of metals, e.g., Mg and Fe, at about 30° C. with shaking.

The cells are thereafter harvested by known techniques, e.g., centrifugation, and washed with cold water, recentrifuged, and suspended in known buffer solutions.

The L-mannose isomerization is carried out by utilizing art recognized procedures to immobilize the cells containing L-mannose isomerase or to rupture the cells, for example, through contact with a lysing agent, such as toluene, or through ultra-sonic treatment. If the cells are ruptured to release the intracellular L-sugar isomerase, a cell-free extract containing the enzyme is obtained by known methods and the extracellular enzyme can be immobilized in accordance with known and conventional procedures. For example, the enzyme can be immobilized on various particulate silica material including glass or ceramic-based materials, natural or synthetic polymers such as cellulose, e.g. diethylaminoethyl cellulose, and various known organic polymer supports known in the art.

The substrate is added to the reaction mixture solution, and the isomerization process is carried out at about 30° C. for a length of time which can be readily determined experimentally. The reaction temperature will be predicated on the thermal stability of the enzyme system employed, the more thermally stable systems permitting higher reaction temperatures. Of course, the reaction time will, in part, be determined by the reaction temperature. As would be expected, the higher the temperature, the shorter the reaction time period for the desired degree of reaction. In enyzmatic reactions of the present type, equilibrium will be reached in reasonable time periods, usually ranging from as little as 30 minutes up to several hours, and even longer. As is recognized in this art, the progress of the reaction can be followed by removal of aliquots from the reaction mixture and analyzing for product and/or starting substrate, thus, permitting optimization of reaction parameters for the specific enzyme system employed. The enzyme system may vary depending on the microorganism from which the enzyme is obtained, and the method of isolation and purification, if employed.

Once equilibrium is established, the isomerization reaction is essentially completed and the enzyme is removed from the reaction mixture solution by art recognized procedures, e.g., by denaturing the enzyme and removing the denatured protein by centrifugation, or separation of immobilized enzyme by physical means, e.g., filtration.

The L-mannose left in the reaction mixture solution is separated from the L-fructose by adding phenylhydrazine to the solution, thereby, causing phenylhydrazones of the L-sugars to form. Due to the difference in solubility in aqueous solution between the L-sugar phenylhydrazones, L-mannose phenylhydrazone crystallizes leaving L-fructose phenylhydrazone in solution. The crystalline precipitate can be removed by filtration, and L-fructose is regenerated from the dissolved phenylhydrazone by known techniques, such as refluxing the filtrate with ethanol, benzaldehyde, or benzoic acid.

If desired, the L-mannose can be left in admixture with L-fructose and the mixture used as, among other things, a sweetening agent.

EXAMPLE

A. Preparation and selection of mutant strains

A 25-ml culture of *Klebsiella aerogenes* in glucose mineral medium containing 0.71% $Na_2HPO_4$, 0.15% $KH_2PO_4$, 0.3% $(NH_4)_2SO_4$, 0.009% $MgSO_4$, 0.0005% $FeSO_4.7H_2O$ and 0.5% glucose is harvested and washed, then resuspended in 5 ml of mineral medium without glucose.

The cells are irradiated with an ultraviolet light source at a distance of about four inches for about eight minutes. The treated cells are recovered and washed by centrifugation, then resuspended with 5 ml of mineral medium without glucose. A 0.5 ml aliquot of the suspension is inoculated into 100 ml of mineral medium with 0.5% glucose and incubated overnight at 30° C. with shaking to allow a 25-50 fold increase in cell number.

Small aliquots (0.1-0.2 ml) of the resulting culture are inoculated onto agar plates containing mineral medium with 0.5% glucose, then incubated for 18-24 hrs. at 30° C. Colonies which appear on these master plates are replica-plated onto fresh agar plates containing the same medium and incubated at 30° C. for 18-24 hrs. A circular disc of filter paper moistened with 0.16M Tris-HCl buffer (pH 7.6) containing 67 mM $CoCl_2$ is pressed down onto the replica plates to pick up the microbial colonies by adsorption. The paper is removed and placed colony-side down onto a second filter paper disc moistened with the above solution plus 10% L-mannose, forming a "sandwich" with microbes between the papers.

The paper sandwich is pressed between two clean glass plates and incubated at 30° C. for a period of time necessary for isomerization of L-mannose to L-fructose to occur. The paper sandwich is disassembled and air-dried. The papers are then sprayed with acidic naphthoresorcinol for ketose detection. The development of pink spots is a positive test for keto-sugar, i.e., L-fructose and, therefore, L-mannose isomerase. Colonies corresponding to these positive zones on the filter paper are then located by reference to the original master plates and isolated by conventional microbiological techniques.

B. Isomerizing L-mannose to L-fructose

Cells of the mutant strain of *Klebsiella aerogenes* having the desired trait are harvested by centrifugation after growing under aerobic conditions for 10-12 hours in 500 ml of mineral medium with glucose at 30° C. with shaking. The cells are then washed with cold water, recentrifuged, and suspended in 15 ml of 20 mM 2-amino-2-(hydroxymethyl)-1,3-propanediol hydrochloride buffer (pH 7.6). They are disrupted in a sonic oscillator equipped with an ice-water cooling jacket and the cellular debris is removed by centrifugation. The remaining supernatant solution is the cell-free extract containing L-mannose isomerase.

The reaction mixture containing 28 mmoles of L-mannose, 5 mmoles of cobalt chloride, 12 mmoles of 2-amino-2-(hydroxymethyl)-1,3-propanediol hydrochloride buffer (pH 7.6), and cell-free extract (300-350 mg of protein) is incubated for 2-3 hours at 30° C., or until equilibrium is established. The reaction mixture is then heated in a boiling water bath, and the denatured protein removed by centrifugation.

L-mannose is separated from L-fructose by adding a solution containing 3.1 g of phenylhydrazine in 7.0 ml of glacial acetic acid, and the resulting mixture is maintained overnight at 4° C. L-mannose phenylhydrazone, unlike L-fructose phenylhydrazone, has low solubility in water and crystallizes. The crystallized phenylhydrazone is removed by suction filtration and the filtrate is concentrated to form a precipitate that is removed by suction filtration.

L-fructose is regenerated from the dissolved phenylhydrazone by refluxing the filtrate for 2 to 3 hours with 13 ml of ethanol, 8 ml of benzaldehyde, and 0.8 g of benzoic acid. Once the suspension is cooled to room temperature, the liquid phase is decanted from the insoluble 2-benzyl-2-phenylhydrazone, washed with three 100-ml portions of chloroform, and decolorized with Darco G-60 carbon. This solution is deionized by passage through a bed of mixed resins column. The neutral effluent is evaporated under reduced pressure to a syrup. The syrup is then dissolved in warm absolute alcohol and nucleated with crystals of L-fructose. After about 24 hours at room temperature, needle-like crystals of L-fructose are collected by gravity filtration.

While the present invention has been described in connection with specific embodiments thereof, it is understood that it is capable of further modifications and adaptions as will be readily understood by those skilled in the art.

I claim:

1. A process for isomerizing L-mannose to L-fructose which comprises contacting L-mannose with L-mannose isomerase produced by a mutant microorganism selected from the group consisting of the genera Escherichia, Lactobacillus, and Klebsiella cultivated in the absence of an inducing sugar.

2. A process according to claim 1, wherein the L-mannose is in the form of an admixture with L-glucose.

3. A process according to claim 1, wherein the microorganism is selected from the group consisting of *Escherichia coli, Lactobacillus planatarium* and *Klebsiella aerogenes.*

4. A process for isomerizing L-mannose to L-fructose which comprises:

(a) subjecting a microorganism selected from the group consisting of the genera Escherichia, Lactobacillus, and Klebsiella to a mutagenizing agent;

(b) isolating a mutant strain of the microorganism having the ability to produce L-mannose isomerase in the absence of an inducing sugar; and (c) isomerizing L-mannose to L-fructose by employing L-mannose isomerase produced from said mutant strain under L-mannose isomerizing conditions.

5. A process for isomerizing L-mannose to L-fructose which comprises contacting L-mannose with L-mannose isomerase produced by a mutant microorganism of the genus Klebsiella cultivated in the absence of an inducing sugar.

6. A process according to claim 5, wherein the miroorganism is *Klebsiella aerogenes.*

* * * * *